(12) United States Patent
Bakhtyari-Nejad-Esfahani

(10) Patent No.: US 11,369,296 B2
(45) Date of Patent: Jun. 28, 2022

(54) NEEDLE HOLDER

(71) Applicant: Olberon Medical Innovation SAS, Lille (FR)

(72) Inventor: Arash Bakhtyari-Nejad-Esfahani, Nottingham (GB)

(*) Notice: Subject to any disclaimer, the term of this patent is extended or adjusted under 35 U.S.C. 154(b) by 297 days.

(21) Appl. No.: 16/163,093

(22) Filed: Oct. 17, 2018

(65) Prior Publication Data
US 2019/0046097 A1 Feb. 14, 2019

Related U.S. Application Data

(63) Continuation of application No. 13/983,043, filed as application No. PCT/GB2012/050023 on Jan. 6, 2012, now abandoned.

(30) Foreign Application Priority Data

Feb. 1, 2011 (GB) ........................... 1101718

(51) Int. Cl.
*A61B 5/15* (2006.01)
*A61B 5/154* (2006.01)

(52) U.S. Cl.
CPC .... *A61B 5/150732* (2013.01); *A61B 5/15003* (2013.01); *A61B 5/154* (2013.01);
(Continued)

(58) Field of Classification Search
CPC .......... A61B 5/150732; A61B 5/15003; A61B 5/150259; A61B 5/150389;
(Continued)

(56) References Cited

U.S. PATENT DOCUMENTS 2,198,666 A   4/1940   Gruskin
2,457,464 A   12/1948  Grose
(Continued)

FOREIGN PATENT DOCUMENTS

CN   201320175 Y   10/2009
CN   201337718 Y   11/2009
(Continued)

OTHER PUBLICATIONS

International Preliminary Report on Patentability for PCT/GB2012/050023 dated Aug. 6, 2013 in 6 pages.
(Continued)

*Primary Examiner* — Patrick Fernandes

(57) ABSTRACT

A medical needle holder (10) having a generally hollow body (18) which extends in the direction of an axis (62) from a first end (20) to a second end (22). The first end is shaped for reception of a needle (50) therein and the second end is open to allow for insertion of a fluid receptacle (16). The first axis is substantially aligned in use with a needle positioned in the first end of the body. The needle holder comprises a grip portion (28) which extends outwardly from the body in a direction which is angularly offset from the first axis. The grip portion may be actuable between an in-use condition and a disposal condition in which the grip portion covers a needle in the needle holder. The body (18) may comprise control formations on its inner surface to allow for control over the insertion of a fluid receptacle (16) into the body.

20 Claims, 4 Drawing Sheets

(52) U.S. Cl.
CPC .. *A61B 5/150259* (2013.01); *A61B 5/150389* (2013.01); *A61B 5/150473* (2013.01); *A61B 5/150687* (2013.01); *A61B 5/150748* (2013.01); *A61B 5/150267* (2013.01); *A61B 5/150351* (2013.01); *A61B 5/150916* (2013.01)

(58) Field of Classification Search
CPC ........ A61B 5/150473; A61B 5/150687; A61B 5/150748; A61B 5/154; A61B 5/150267; A61B 5/150351; A61B 5/150916; A61B 5/15
See application file for complete search history.

(56) References Cited

U.S. PATENT DOCUMENTS

| | | | |
|---|---|---|---|
| 3,324,854 A | 6/1967 | Weese | |
| 3,500,821 A | 3/1970 | Ogle | |
| 4,299,219 A | 11/1981 | Norris, Jr. | |
| 4,320,769 A | 3/1982 | Eichhorn et al. | |
| 4,332,248 A | 6/1982 | DeVitis | |
| 4,393,870 A | 7/1983 | Wagner | |
| 4,576,168 A | 3/1986 | Jalowayski | |
| 4,586,924 A | 5/1986 | Lanning | |
| 4,619,248 A | 10/1986 | Walsh | |
| 4,638,792 A | 1/1987 | Burgin | |
| 4,664,651 A | 5/1987 | Weinshenker | |
| 4,924,878 A | 5/1990 | Nottke | |
| 4,944,308 A | 7/1990 | Akerfeldt | |
| 5,070,884 A | 12/1991 | Columbus et al. | |
| 5,275,299 A | 1/1994 | Konrad et al. | |
| 5,312,361 A | 5/1994 | Zadini et al. | |
| 5,320,607 A | 6/1994 | Ishibashi | |
| 5,364,362 A | 11/1994 | Schulz | |
| 5,415,647 A | 5/1995 | Pisarik | |
| 5,478,315 A | 12/1995 | Brothers et al. | |
| 5,538,010 A | 7/1996 | Darr et al. | |
| 5,680,872 A | 10/1997 | Sesekura et al. | |
| 5,733,265 A | 3/1998 | Bachman et al. | |
| 5,902,273 A | 5/1999 | Yang et al. | |
| 5,967,991 A | 10/1999 | Gardineer et al. | |
| 5,984,890 A | 11/1999 | Gast et al. | |
| 6,048,321 A | 4/2000 | McPherson et al. | |
| 6,254,580 B1 | 7/2001 | Svedman | |
| 6,394,984 B1 | 5/2002 | Hill | |
| 6,814,737 B2 | 11/2004 | Cauthen | |
| 7,428,773 B2 | 9/2008 | Newby et al. | |
| 8,758,300 B2 | 6/2014 | Bakhtyari-Nejad-Esfahani | |
| 2001/0039401 A1 | 11/2001 | Ferguson et al. | |
| 2001/0044606 A1 | 11/2001 | Inkpen et al. | |
| 2002/0049391 A1 | 4/2002 | Kuracina et al. | |
| 2002/0072715 A1 | 6/2002 | Newby et al. | |
| 2002/0077599 A1 | 6/2002 | Wojcik | |
| 2002/0183742 A1 | 12/2002 | Carmel et al. | |
| 2003/0073952 A1 | 4/2003 | Flaherty et al. | |
| 2003/0181860 A1 | 9/2003 | Swenson | |
| 2003/0181861 A1* | 9/2003 | Wilkinson | A61B 5/150587 604/192 |
| 2003/0181874 A1 | 9/2003 | Bressler et al. | |
| 2004/0106903 A1 | 6/2004 | Shue et al. | |
| 2004/0199140 A1 | 10/2004 | Rue et al. | |
| 2005/0148942 A1 | 7/2005 | Newby et al. | |
| 2006/0200078 A1 | 9/2006 | Konrad | |
| 2007/0021724 A1* | 1/2007 | Bressler | A61M 25/0631 604/263 |
| 2007/0026111 A1 | 2/2007 | Cook | |
| 2007/0032741 A1 | 2/2007 | Hibner et al. | |
| 2008/0223815 A1 | 9/2008 | Konrad | |
| 2009/0209912 A1 | 8/2009 | Keyser et al. | |
| 2009/0259143 A1* | 10/2009 | Bakhtyari-Nejad-Esfahani | A61M 5/3287 600/573 |
| 2010/0049241 A1 | 2/2010 | Persson | |
| 2010/0137799 A1 | 6/2010 | Imai | |
| 2010/0160817 A1 | 6/2010 | Parihar et al. | |
| 2012/0130414 A1 | 5/2012 | Birkill et al. | |
| 2013/0310707 A1 | 11/2013 | Bakhtyari-Nejad-Esfahani | |
| 2015/0359560 A1 | 12/2015 | Bakhtyari-Nejad-Esfahani | |

FOREIGN PATENT DOCUMENTS

| | | |
|---|---|---|
| DE | 2501145 | 7/1976 |
| DE | 19620314 A1 | 11/1997 |
| DE | 19647977 A1 | 5/1998 |
| DE | 10 2005 054989 | 5/2007 |
| EP | 0453251 B1 | 8/1997 |
| EP | 0569835 B1 | 9/1998 |
| EP | 0867378 B1 | 10/2002 |
| EP | 1 306 097 | 5/2003 |
| EP | 1 346 742 | 9/2003 |
| EP | 1944051 A1 | 7/2008 |
| EP | 1 587 419 | 11/2009 |
| EP | 2679188 B1 | 12/2015 |
| FR | 542914 A | 8/1922 |
| FR | 2612401 A | 9/1988 |
| FR | 2698778 B1 | 8/1995 |
| GB | 553728 A | 3/1946 |
| GB | 1256524 A | 12/1971 |
| GB | 1036000 | 7/1996 |
| GB | 2301035 A | 11/1996 |
| GB | 2367895 A | 4/2002 |
| GB | 2438518 | 11/2007 |
| GB | 2436526 B | 1/2010 |
| JP | 2007-167578 | 7/2007 |
| RU | 2109525 C1 | 4/1998 |
| WO | WO 95/07722 | 3/1995 |
| WO | WO 98/25512 | 6/1998 |
| WO | WO 01/34019 | 5/2001 |
| WO | WO 2003/003908 | 1/2003 |
| WO | WO 2004/066840 | 8/2004 |
| WO | WO 2006/007629 | 1/2006 |
| WO | WO 2006/054280 | 5/2006 |
| WO | WO 2007/139741 | 12/2007 |
| WO | WO 2008/024684 | 2/2008 |
| WO | WO 2008/085393 | 7/2008 |
| WO | WO 2009/021170 | 2/2009 |
| WO | WO 2014/118376 | 8/2014 |

OTHER PUBLICATIONS

International Search Report for PCT/GB2012/050023 dated Mar. 21, 2012, in 4 pages.

Search Report issued for Great Britain Appl. No. GB1101718.3, dated Apr. 28, 2011.

Search Report issued for Great Britain Appl. No. GB1112933.5, dated Nov. 4, 2011.

* cited by examiner

NEEDLE HOLDER

FIELD

The present invention relates to a needle holder and more particularly, although not exclusively, to a holder for a medical needle which may be used for insertion of a needle into a vessel of a patient.

BACKGROUND

It is known to provide a needle holder to support a needle for insertion into a vessel of a patient. A needle holder also provides a support structure, by which one or more further members may be held in fluid communication with the vessel via the needle.

Such needle holders are used, for example, when drawing blood from a patient. A conventional holder takes the form of a generally tubular structure having an open end and a formation at the opposing end for reception of a needle. The needle is typically held by the holder part way along its length such that needle extends part way into the tubular portion of the holder.

Using this arrangement, a further member can be inserted into the open end of the tubular structure so as to form a fluid connection with the needle within the holder. Such an arrangement is described for example in International Patent Application PCT/US2007/026111 (published as WO2008/085393).

When taking blood from a patient, a phlebotomist will typically insert the free end of the needle into a blood vessel, such as a vein, and subsequently insert an evacuated tube or vial into the open end of the holder for communication with the opposing end of the needle. The negative pressure in the collection tube draws blood through the needle. The tube is subsequently removed and sealed so as to provide a blood sample. Further tubes may be connected in turn depending on the number of discrete samples or volume of fluid to be drawn.

It has been noted by the inventor that a phlebotomist will typically insert the needle using their preferred hand, depending on whether they are right or left-handed, since careful positioning of the needle is required for insertion into a desired blood vessel. However the phlebotomist will often swap hands in order support the needle holder with their other hand whilst picking up and inserting a blood collection tube. Such a procedure is awkward and can disturb the needle.

Furthermore, the connection of a tube to the needle conventionally requires the tube to be pushed against the needle in the direction of the needle axis so as to puncture a seal on the tube. The seal will typically resist the manual application of such a force in a generally predictable manner up to the point of yield, at which point the resistance offered by the seal suddenly diminishes. Again, this can lead to movement of the needle, which can cause the free end of the needle be removed from the blood vessel.

Once the desired sample has been collected, a phlebotomist is required to both support the needle holder and remove the tube there-from. This action can disturb the needle if the holder is not adequately supported.

Any movement and/or subsequent repositioning of the needle for the above reasons is generally undesirable and can cause discomfort to the patient.

It has also been observed that a blood vessel, such as a vein, can collapse when blood is drawn, with has the effect of reducing the depth of the blood vessel. This increases the accuracy with which the needle must be positioned and held in order to remain in the vessel. Repositioning of the needle may be required in such an event.

Once removed from the patient, the exposed needle also poses a hazard to the phlebotomist or subsequent handlers.

SUMMARY

It is an aim of the present invention to provide an improved needle holder which mitigates one or more of the above-described problems. It may be considered to be an aim of the present invention to provide a needle holder which is less susceptible to unwanted movement in use.

According to one aspect of the present invention there is provided a needle holder having a generally hollow body which extends in the direction of a first axis from a first end shaped for reception of a needle therein to a second end which is open, the first axis being substantially aligned in use with a needle positioned in the first end of the body, wherein the needle holder comprises a grip portion which extends outwardly from the body in the direction of a second axis, the second axis being angularly offset from the first axis.

The provision of a grip portion of this type has been found to allow for improved manual support and positioning of the needle holder relative to a patient. The improved level of support is particularly beneficial in the event that it is required to connect or move other members relative to the open end of the needle holder in use. One application for such a needle holder is for drawing fluid from a patient.

The first axis may be an axis of revolution of the hollow body. The angular offset between the first and second axis may be greater than 30° and typically greater than 45°. The second axis may be substantially perpendicular to the first axis. The grip portion may extend substantially radially outwardly from the first axis. In one embodiment the grip portion may be shaped or oriented such that it is sloped or angled towards the second end of the body. The grip portion may depend from the region of the first end of the body. The grip portion may have grip formations, such as, for example, one or more depressions, which face forward or towards the first end of the body. The grip portion may have opposing sides with opposing grip formations. The grip portion may be sloped at its front edge.

In use, the grip portion is positioned such that it can be comfortably held, for example, between a thumb and finger of a user from the front (or needle end) of the holder. In this manner the holder can be supported by hand close to the point at which a needle is inserted to a patient, leaving the second, rear end of the holder free and easily accessible. Supporting the needle in this manner naturally resists forces which may be applied in use in the direction of the needle axis. The rearward slope of the grip is also beneficial in that the needle holder is generally held at an angle relative to a patient's skin. Thus the grip portion may extend generally perpendicularly from the patient's body in the vicinity of the point of insertion of the needle, when the needle holder is oriented for use.

The angular offset between the grip portion and the body may be complimentary with the angle at which the needle or needle holder is typically oriented for use. This angle of use may vary between different uses but is typically between 10° and 40°, such that the angular offset between the first and second axes is between 50° and 90°.

The grip portion may be substantially hollow and/or open-sided. The grip portion may be open towards the first end of the body.

In one embodiment, the needle holder comprises a guard member having a guide surface adapted to rest against a patient's skin. The first end of the body may be arranged to provide a needle holding formation which holds a needle in a fixed orientation relative to the guide surface. The guard member may depend from the body. The guard member may protrude from the body in a direction different to or opposite to that of the grip portion. The guide surface may be offset from the first axis by between 10° and 40°. The guard member and/or guide surface may be of length between a quarter and three quarters of the length of the body. The guard member and/or guide surface may protrude forwardly of the first end of the body.

A plurality of guard members may be provided. A pair of guard members may be provided on opposing sides of a needle holding formation at the first end of the body.

The guard members both facilitate insertion of the needle and also support the needle in a desired orientation once inserted. The combination of the guard member and grip portion provide for a needle holder which is less prone to unwanted movement during use.

In one embodiment the body is shaped to receive a fluid receptacle. The body may be shaped to form a releasable push-fit or friction-fit connection with a fluid receptacle. The body may have one or more receptacle reception formations thereon. The body may be generally tubular in shape.

The first end of the body may comprise an end wall having an opening therein for reception of a needle. The end wall may comprise a connection formation about said opening which may comprise a neck or collar.

According to one embodiment, the grip portion may be actuable relative to the body between a first condition in which the grip portion extends in the direction of the second axis and a second condition in which the grip portion is arranged about the first axis. The first condition may comprise an in-use condition. The second condition may comprise a storage or disposal condition.

The needle holder may be made safe before or after use by orienting the grip portion in the second condition. The grip portion may be pivotally or slidably mounted to the body portion. One of the grip portion or body may comprise one or more pivot formations. The other of the grip portion and body may comprise a corresponding recess for reception of the pivot formation.

The grip portion may comprise opposing side walls and an adjoining wall there-between. One side of the grip portion may be open. The grip portion may be moveable relative to the body in use such that a needle can pass through the open side of the grip portion. A needle attached to the body may be disposed between the side walls of the grip portion in the second position.

The needle holder may comprise a releasable fastener for maintaining the grip portion in the first condition. The grip portion or body may comprise a catch or latch.

The needle holder may comprise a fastener for maintaining the grip portion in the second condition. This fastener may comprise a non-return fastener, which may take the form of a formation on the grip portion or body. The formation may comprise a recess or stop member having a first ramped surface to allow relative movement between the grip member and body in a first direction and a second surface which is arranged to prevent return motion once the grip portion has achieved the second condition. The second surface may comprise a stop surface.

In one embodiment, the needle holder has one or more control formations. The, or each, control formation may be formed on an inner surface of the body. The, or each, control formation may be shaped for cooperation with one or more corresponding formations on a fluid receptacle to be inserted into the body in use. The, or each, control formation may be arranged obliquely to the first axis. The, or each, control formation may be arranged to limit the degree of axial movement available to the fluid receptacle within the body. The, or each, control formation may be arranged to convert a rotational force or torque applied to the fluid receptacle into motion of the fluid receptacle relative to the body in the direction of the first axis.

The, or each, control formation may be generally helical in shape and may comprise a portion of a helix. The, or each, control formation may comprise a thread or partial thread formation. A plurality of control formations may be provided about an inner circumferential wall of the body. The start of one control formation may overlap in a circumferential direction with the end of an adjacent control formation.

The use of such control formations can avoid the need for the fluid receptacle, such as, for example, an evacuated tube, to be pushed in the direction of the needle axis in order to puncture the receptacle seal. Instead the receptacle can be actuated in a rotational sense to break the seal and thereby avoid or minimise unwanted axial movement of the needle in use. The orientation of the control formations means that the component of the applied force in the direction of the first axis is, at least in part, resolved within the body by a corresponding reaction force such that it is not communicated to the needle.

According to a second aspect of the present invention, there is provided a needle device comprising a needle holder according to the first aspect and a needle or needle assembly attached to the needle holder such that the needle extends substantially in the direction of the first axis from a free end which is outside of the body to an opposing end which is in the interior of the body.

The needle or needle assembly may be supported part way along its length by the first end of the body.

A fluid receptacle may be insertable into the second end of the needle holder body in use. The fluid receptacle may be evacuated or partially evacuated. Alternatively the fluid receptacle may contain fluid to be administered to a patient and may be positively pressurised. The fluid receptacle typically has a seal which is arranged to be punctured by the end of the needle in use. The seal may be formed of a resilient material such that it coapts with the needle once punctured so as to form a seal around the needle once punctured.

The fluid receptacle may have corresponding control formations for cooperation with control formations on the needle holder body.

According to a third aspect of the present invention, there is provided a needle holder having a generally hollow body which extends in the direction of an axis from a first end shaped for reception of a needle therein to a second end which is open, the first axis being substantially aligned in use with a needle positioned in the first end of the body, wherein the body comprises an inner surface having a control formation thereon, said control formation being arranged obliquely to the axis so as to control travel of a fluid receptacle along the body in the direction of the axis in use.

According to a fourth aspect of the invention, there is provided a fluid receptacle having one or more control formations thereon which correspond to the control formation on the body of the needle holder according to the thirst aspect.

Any, or any combination of, the needle holder, the needle and/or the fluid receptacle of the third or fourth aspects may comprise any of the optional features defined above in relation to the first or second aspects.

BRIEF DESCRIPTION OF THE DRAWINGS

Practicable embodiments of the invention are described in further detail below with reference to the accompanying drawings, of which.

DETAILED DESCRIPTION

Figure 1:
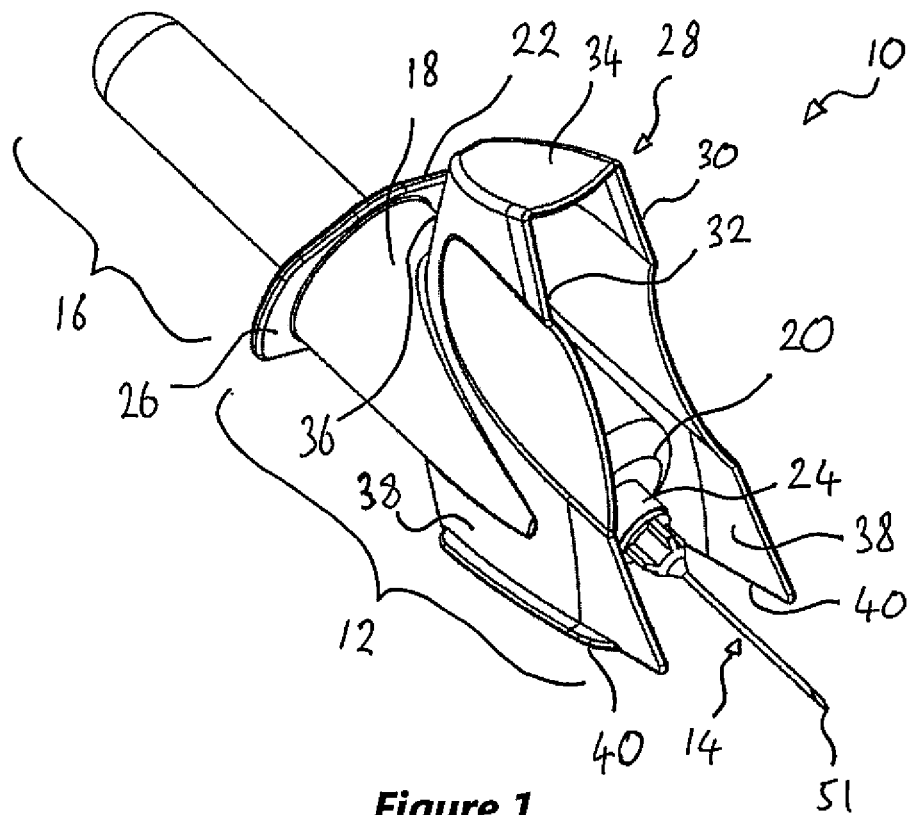
FIG. 1 shows a three-dimensional view of a needle holder according to one embodiment of the present invention with a needle and fluid receptacle attached thereto for use.

The invention provides for a needle holder and associated needle device having formations for improved support and/or actuation during use. The needle holder and device are particularly suited to phlebotomy applications, although other applications involving the drawing or delivery of fluids to vessels within the body may be encompassed.

Figure 2:
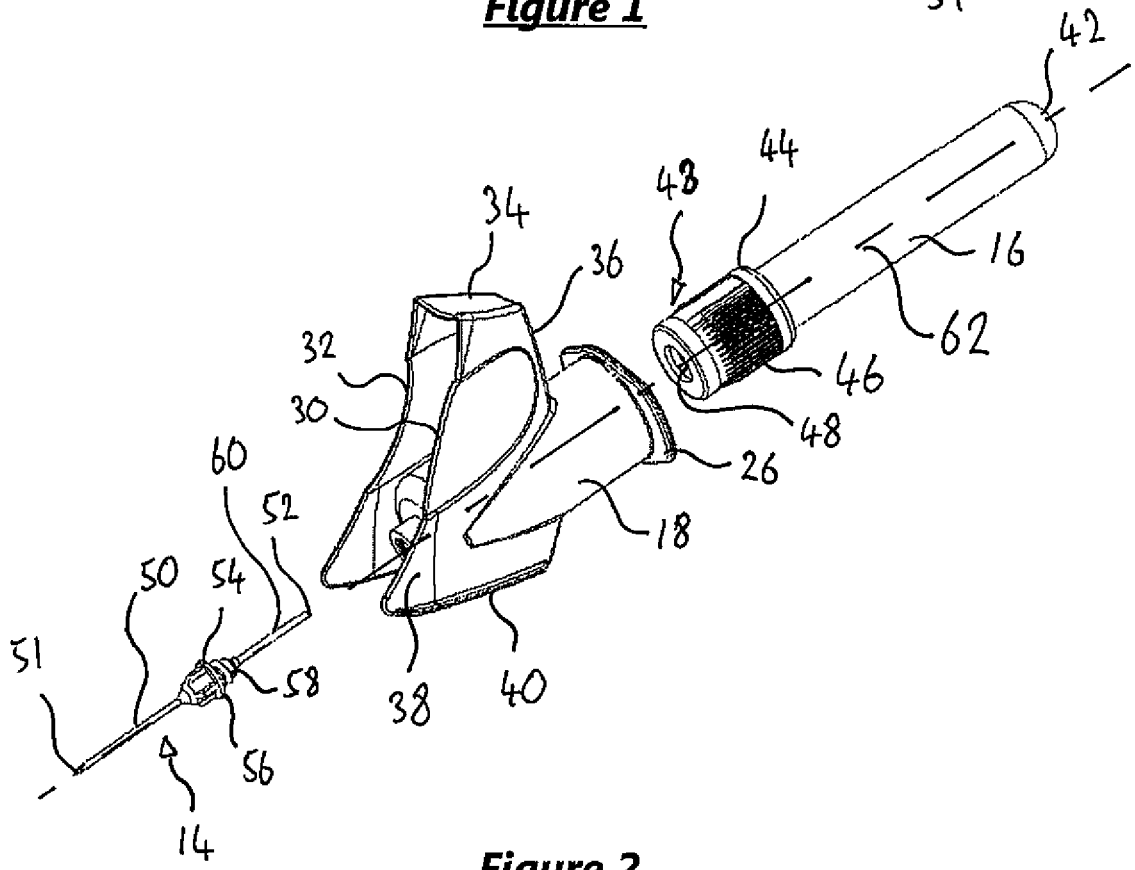
FIG. 2 shows an exploded three-dimensional view of the embodiment of FIG. 1.

Turning to FIGS. 1 and 2, there is shown a device 10, in use, generally comprising a needle holder 12, a needle assembly 14 and a fluid receptacle 16.

The needle holder 12 comprises a generally tubular body portion 18 having a first end 20 and an opposing end 22. The first end 20 comprises an end wall which has a central opening within which the needle assembly 14 is insertable. The end wall has a collar formation 24 protruding outwardly there-from to aid correct alignment and retention of the needle assembly in the needle holder in use.

The opposing end 22 is open so as to define an opening which is generally circular in plan. The opening leads to an internal passage within the body portion which is of substantially constant diameter along its length. A flange 26 is provided about the opening at end 22.

A grip portion 28 depends from the body portion 12 and is spaced from the end 22 of the body portion. The grip portion 28 comprises opposing side walls 30 and 32, a top wall 34 and a rear wall 36. The top and rear walls adjoin the side walls of the grip portion so as to define a partially enclosed space within the grip portion. In this regard the grip portion is open to the front or first end 20 of the needle holder.

The side walls 30 and 32 are arranged on either side of the collar 24 and the needle assembly 14 therein. The side walls 30, 32 have opposing grip formations therein, which take the form of a depression in each side wall. Each depression is curved in shape and extends from a leading edge of the corresponding side wall rearward and terminates a short distance from the rear wall 36. Accordingly, each grip formation may be considered to face forward (i.e. towards the needle end of the device).

The side walls 30, 32 are shaped so as to protrude forward of the body portion end wall 20. The side walls 30, 32 extend from a location above the body portion in use generally downwardly on opposing sides of the body portion 18 and terminate below the body portion at guide surfaces 40. The portion of the side walls extending forwardly and below the body portion 18 can be considered to constitute guard members 38, the function of which will be described below. The guard members may be shaped to provide a ridge of material at the guide surface 40 such that the width of the guide surface is greater than that of the remainder of the guard member 38. Such a ridge of material may be considered to constitute a foot portion which extends along a majority of the length of the guard members 38.

The guard members are shaped such that the guide surfaces 40 are approximately a third of the length of the assembled device. Between a quarter and a half of the length of the guide surfaces 40 may protrude forwardly of the body end 20.

The grip portion 28, including the side walls 30, 32 and corresponding guard members 38 may be integrally formed with the body portion, for example by a moulding process. The needle holder 12 is typically formed of a plastics material. In an alternative embodiment, the body portion 18 and grip portion 28 could be formed separately and subsequently attached together for use.

A fluid receptacle 16 is inserted into the open end 22 of the body portion 18 for use. In this embodiment, the fluid receptacle 16 takes the form of a tube or vial which is closed at one end 42 and capable of holding fluid therein. Towards the end 43 of the fluid receptacle 16 which is insertable into the needle holder 28, there is provided a collar 44 having a plurality of friction members in the form of splines 46 longitudinally aligned with the tube 26.

At the end 43 there is provided a seal member in the form of a bung or stopper 48 so as to seal the interior of the tube from the outside. The bung 48 is typically formed of a resilient, elastic material, which may display rubber-like physical properties.

The fluid receptacle in this embodiment is at least partially evacuated such that the pressure in the receptacle is lower than ambient. Such a receptacle is used to draw fluid, typically blood, from a vessel, such as a vein. However the present invention may also be used in conjunction with fluid receptacles which are not evacuated. Such alternative receptacles may be filled or partially filled with fluid to be administered to a patient and may take the form of cartridges, tubes, vials or the like. Such receptacles may be positively pressurised.

The needle assembly 14 comprises a needle 50 having first 51 and second 52 ends. An attachment formation 54 is fixed about the needle 50 part way along its length and comprises a stop member 56 for abutment against collar 24 in use and a fixture 58 arranged for insertion into the collar 24 so as to hold the needle fast against the body 18 in use. The fixture may comprise a screw thread or other similar fixing formation which may correspond to the interior surface of the collar 24.

A sheath 60 extends rearward of the attachment formation 54 and covers the portion of the needle behind the formation 54. The sheath is formed of a polymer material. The rearward end 52 of the needle 14 is insertable into the needle holder 12 and the tube 16 in use.

The needle 51, when assembled, and the associated axis 62 is at an angle typically between 10 and 20° degrees from plane of the guide surfaces 40. In this embodiment, the angle is substantially 15°.

When the device 10 is assembled as shown in FIG. 1, the needle assembly, body portion 18 and fluid receptacle 16 are all aligned with a common axis 62 (shown in FIG. 2), which extends substantially along the length of the needle 50 and which provides a generally central axis for the internal cavity of the body portion 18 and the fluid receptacle 16.

The needle end 51 is considered to be facing forwards and the ends 22 and 42 of the needle holder 12 and fluid receptacle 16 respectively are considered to face rearwards. In the orientation shown, the top surface 34 is considered to be uppermost and the guide surfaces 40 the lower surfaces of the device. It will be appreciated that all references to such orientations and directions are specific to one preferred orientation of the device only and are used merely to aid a reader in understanding the relative features of the device and its use. Such terms should be construed accordingly in the event that the device is oriented differently.

In use, the needle assembly 14 is located relative to the body portion 18 such that the end 51 of the needle 50 protrudes forwardly of the body end 20 and the forward-most portion of the guard members 38. The rear end 52 of the needle within the sheath 60 protrudes into the interior of the body portion 18. At this stage the fluid receptacle 16 is not attached to the device 10.

The device is positioned on a patient's skin such that the guide surfaces 40 rest on the skin surface close to the injection site. The side walls 30, 32 of the grip portion 28 are gripped between the thumb and one or more fingers of the user. The device is slid forward a small distance, in the region of 2-3 mm, such that the tip 51 of the needle pierces the skin at the desired angle of approximately 15°.

The tip of the needle may thus enter a blood vessel. In this position, the device is steady on the user's skin since it is supported by the guide surfaces 40.

The fluid receptacle 6 is then inserted into the body portion 18 in a direction which is generally parallel with the axis 62 such that the rear end 52 of the needle pierces the bung 48. The entry of the needle end 52 into the bung 48 causes the sheath 60 to be retracted over the needle 50. The end 52 of the needle is therefore exposed once the needle has pierced through the bung 48 so as to allow fluid communication between the needle end 51 located in a blood vessel and the inside of the tube 16 via the opposing end 52 of the needle. The material properties of the bung 48 mean that the bung seals about the needle 50 therein.

The negative pressure in the tube 16 draws fluid from the blood vessel into the tube via the needle 50. Once sufficient fluid has been drawn into the tube to negate the pressure differential between the tube and the patient's blood vessel, the tube 16 can be withdrawn from the rear end of the holder 12. Further tubes can be attached in sequence, if necessary, to draw more fluid and subsequently removed as described above. As described above, positively pressurised tubes 16 may also be used with the device 10. It is possible that, after blood has been drawn using tube 16, a fluid could be administered to a patient by removing the tube 16 and replacing it with a fluid-filled receptacle without removing the needle holder.

During the above process, the grip portion 28 can be stably and reliably held by a user, such as a phlebotomist, such that the device 10 is not prone to unwanted movement. In the event that it is necessary to reposition the needle, accurate adjustments can be made by sliding the needle holder back and/or forth on the guide surfaces 40 such that the desired angle of insertion of the needle 50 is maintained.

Once sufficient fluid has been drawn, the needle holder 12 is then slid in a rearward direction on the guide surfaces 40 until the end 51 of needle 50 is removed from the patient's skin. The device 10 can then be lifted off the patient entirely.

Further embodiments of the invention are described below with reference to FIGS. 3 to 8. Those embodiments are similar to the embodiment of FIGS. 1 and 2 described above and like features are not repeated for conciseness.

Accordingly, the above description applies to the embodiments of FIGS. 3 to 8, save for the alternative or conflicting features described below.

In FIGS. 3 to 6, the needle holder 12 has a body portion 18A which is not integral with the grip portion 28A. That is to say, the body 18A and grip 28A portions take the form of separate components which fit together for use.

The side walls 30A and 32A each have an opening in the form of a port 64 which is generally circular in plan. The side walls 30A and 32A in the vicinity of the ports 64 are spaced by a distance which is approximately equal to the diameter of the body portion 18A. The side walls 30A and 32A are each spaced from their associated guard member 38A by a substantially V-shaped cut out. The port 64 is located at or adjacent the apex of the V-shaped cut-out.

Either, or both, side walls 30A, 32A of the grip portion 28A have a latch formation therein. In this embodiment, the latch formation takes the form of an indentation 66 within the side wall. The indentation 66 is located in a rearward facing edge of the V-shaped cut-out.

The body portion 18A has a pair of projections towards it front end and positioned on opposing sides thereof. The projections are aligned and take the form of pivot members 68. The pivot members 68 are arranged for location within the ports 64 of the grip portion when assembled for use.

The body formation 18A has a latch formation 70, which is arranged for cooperation with the corresponding latch formation 66 in the grip portion. A pair of latch formations 70 may be provided on opposing sides of the body 18A. In this embodiment, the latch formation takes the form of a projection having a ramped surface and a blunt end.

Figure 3:
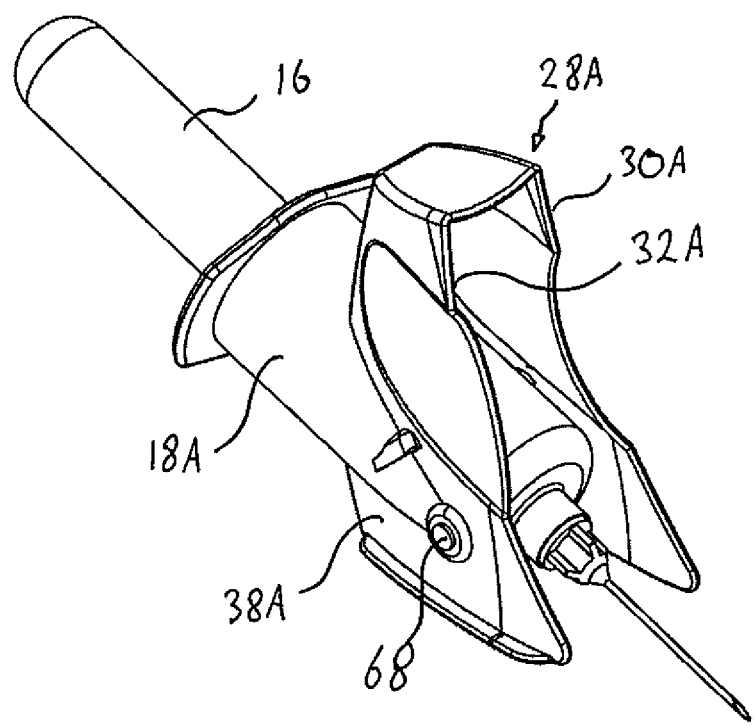
FIG. 3 shows a three-dimensional view of a needle holder according to a second embodiment of the present invention with a needle and fluid receptacle attached thereto for use.
Figure 4:
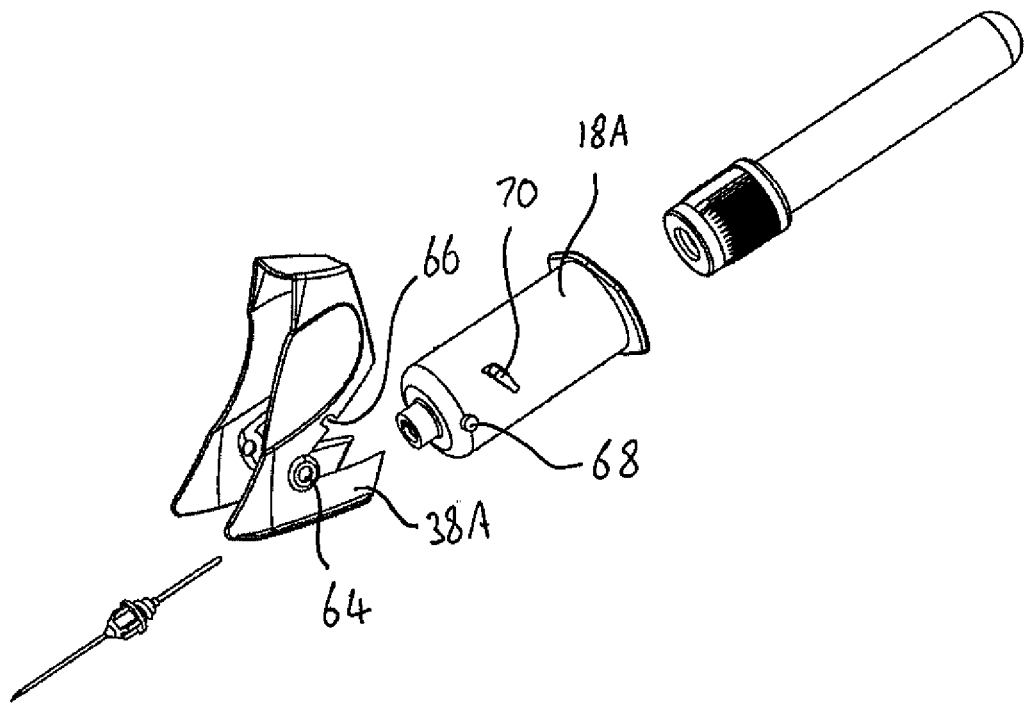
FIG. 4 shows an exploded three-dimensional view of the embodiment of FIG. 3.
Figure 5:
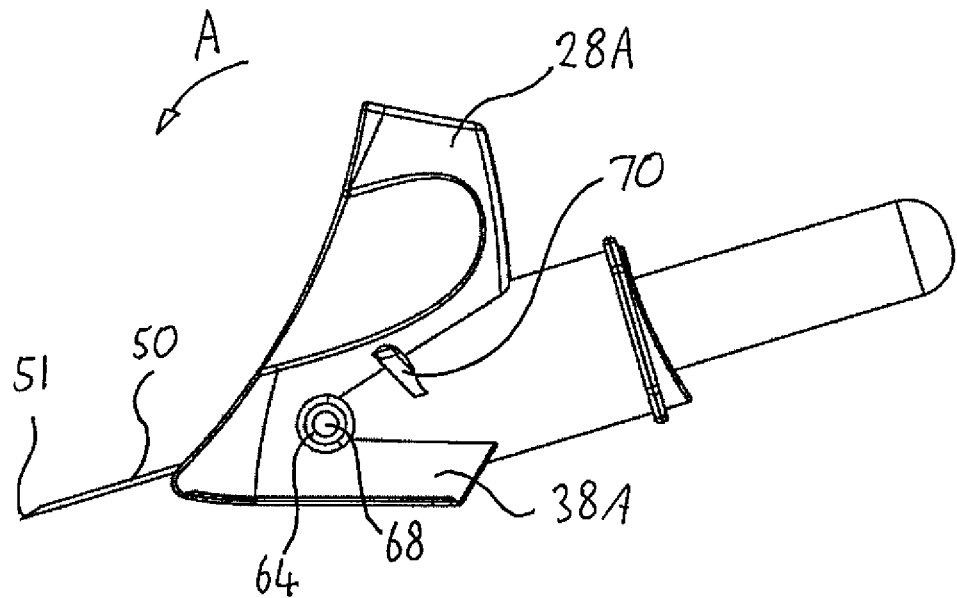
FIG. 5 shows a side view of the embodiment of FIG. 3 in an in-use condition.
Figure 6:
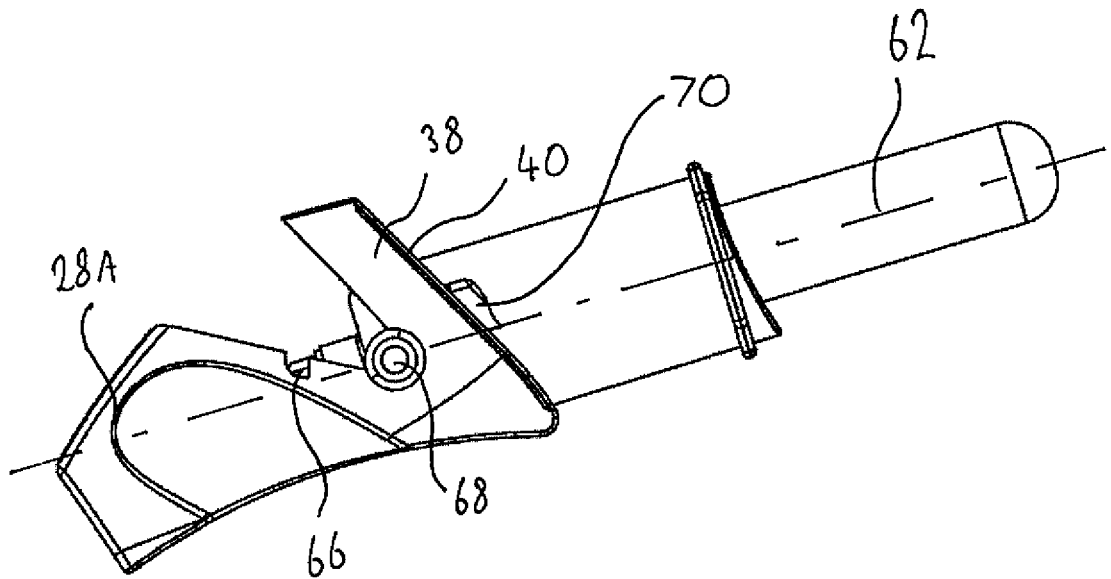
FIG. 6 shows a side view of the embodiment of FIG. 3 in a disposal condition.

FIGS. 5 and 6 show the device of FIGS. 3 and 4 in different conditions. In FIG. 3 the device is arranged in a first, or in-use, condition. The pivots 68 of the body 18A are located in the ports 64 of the grip portion. In this condition the grip portion is substantially upstanding form the body portion in a manner as described above in relation to FIGS. 1 and 2. The body and grip portions are held in this condition by the engagement of the latching projections 70 in the indentations 66 of the grip portion. The projection 70 and indentations are shaped so as to engage in a click-fit or friction fit type of engagement. This condition is used for the positioning and insertion of the needle into a patient.

Once the device has been removed from the patient, the device can be 'made safe' by pivoting the grip portion forward, in the direction of arrow A, out of engagement with the latching formation 70. This requires application of a force sufficient to disengage the latching engagement between the protection 70 and indentation 66. The continued pivoting actuation of the grip portion 28A in the direction of arrow A causes the guard members 38A to ride up and over the ramped surface of the projections 70. At the same time, the side walls 30A and 32A are brought over the needle 50 such that the needle is covered by the grip portion 28A as shown in FIG. 6.

The condition shown in FIG. 6 represents a storage or disposal condition of the device. The grip portion is generally aligned with the device axis 62. In this condition the needle is held within the interior of the grip portion 28A such that the needle 50, and in particular the needle end 51, is not exposed. This greatly reduces the likelihood of the needle accidentally puncturing the skin of anyone subsequently handling the device or a receptacle in which the device is located.

Once the guard members 38 have passed over the projection 70, they are prevented from actuation in a return direction by abutment of the guide surfaces 40 against a bluff side of the projection 70. This arrangement may be considered to provide for a non-return or single use device which is to be disposed of after it has been made safe as described above. In this regard, the connection between the latch projection 70 and the indentation 66 may be frangible.

Figure 7:
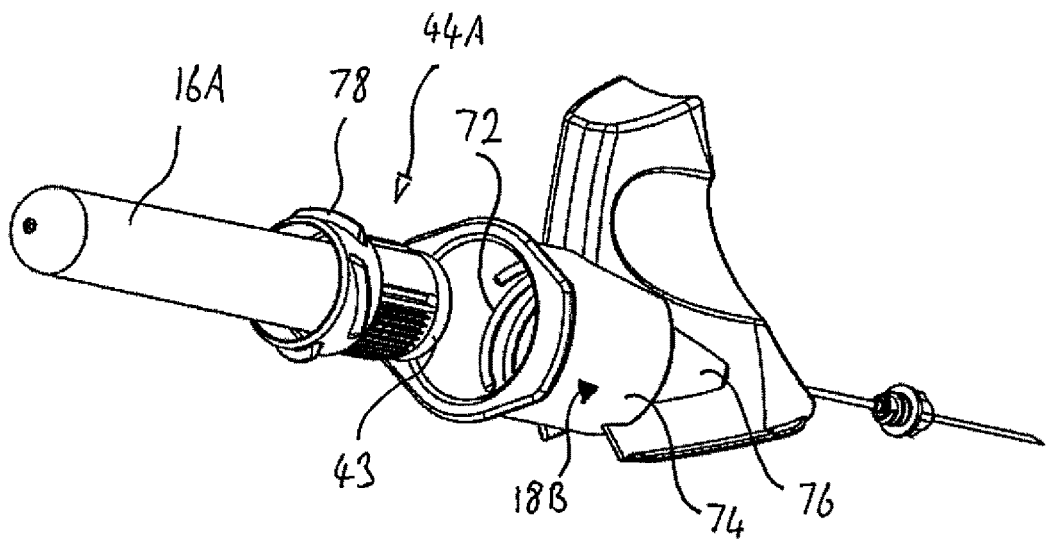
FIG. 7 shows a three-dimensional view of a needle holder according to a third embodiment of the present invention; and, FIG. 8 shows three stages of actuation of a needle holder and fluid receptacle according to a fourth embodiment of the present invention.
Figure 8:
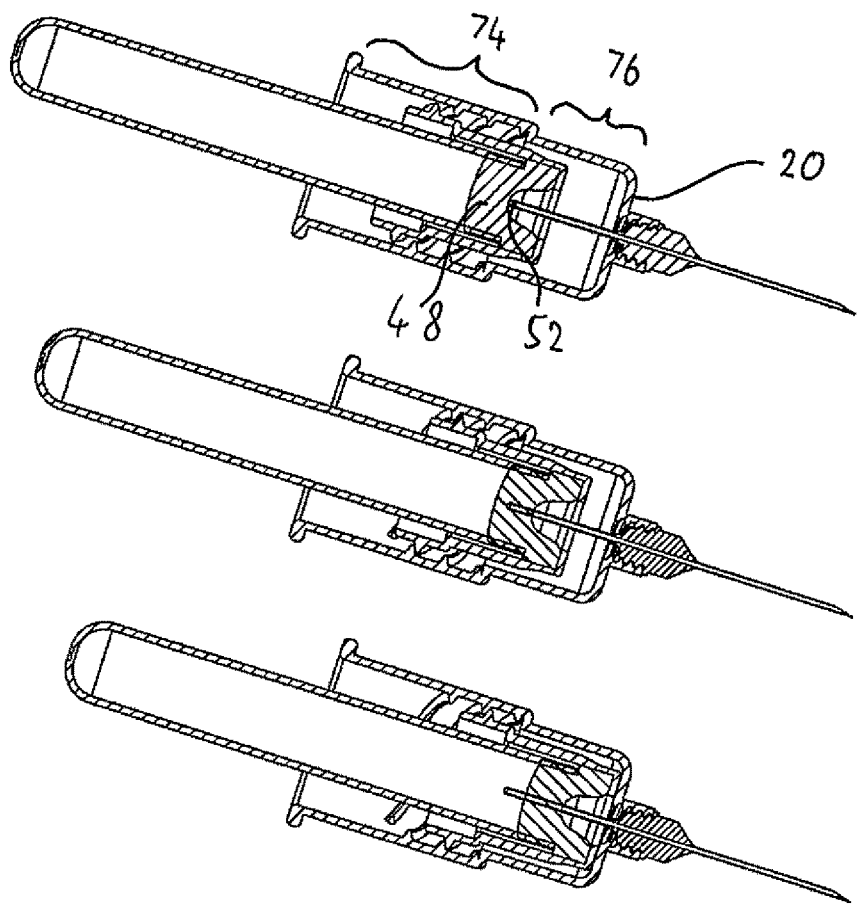

Turning now to FIGS. 7 and 8, there is shown a further embodiment of the invention. In FIG. 7 the features of this embodiment are shown in conjunction with a device as shown in FIGS. 1 and 2. However this embodiment may also be used in conjunction with a device as shown in FIGS. 3 to 6.

In FIGS. 7 and 8, the body portion 18B has a plurality of formations 72 on its interior surface. Each formation 72 depends inwardly from the wall of the body portion 18B. The formations are elongate in form and substantially helically arranged. In this embodiment, each formation is a part helix.

The arrangement of helical formation is such that a tail end of one formation overlaps with a leading end of an adjacent formation. Four such formations are provided in this embodiment. Whilst the arrangement of formations may be described as being threaded, it is to be understood that the formations differ from a conventional thread which is used for fastening male and female parts in that such a conventional arrangement typically comprises a single, continuous thread. Also the formations 72 of this embodiment are typically arranged at a greater angle to the axis 62 than would be normal for a conventional screw thread.

The body portion 18B also differs from the body portion 18 of FIG. 1 in that it comprises two sections, 74 and 76. Section 74 is a rearward section of greater diameter and section 74 is forward section having a smaller diameter. Section 74 encompasses the first end 20 of the body portion. Sections 74 and 76 are joined by an intermediate wall in the form of a circumferential rim. Sections 74 and 76 are typically integrally formed by a moulding process.

The helical formations 72 are located in section 74. And depend inwardly to an internal diameter which is equal to or slightly larger than the diameter of section 76.

The fluid receptacle 16A in this embodiment has corresponding formations 78 formed on an outer surface of collar 44A. Four upstanding helical formations 78 are provided and are angled to correspond to the shape of formations 72 in the body portion. However, whilst the formations 78 are elongate in form, each formation is shorter in length than the formations 72 such that the ends thereof do not overlap. The formations 72 are equally spaced about the perimeter of the collar 44A.

The collar 44A has sections 80 and 82. Section 80 is larger in diameter and is rearward of section 82. The formations 78 are located on section 80. Section 82 is located towards the end 43 of the fluid receptacle 16A to be inserted in the body portion 18B in use. Section 82 is similar to the collar 44 described above in relation to FIG. 2 and has axial splines 46 about its perimeter.

In the upper, middle and lower views of FIG. 8, the fluid receptacle 16A and body portion 18B are shown at different stages of use. In the upper view, the collar end of the fluid receptacle 16A has been inserted into the end 52 of the needle 50 is just short of, or touching, the bung 48. The formations 72 and 78 are arranged such that this condition occurs upon contact there-between.

The diameters of the formations 72 and 78 are such that the formations interfere and prevent further entry of the fluid receptacle 16A into the body portion 18B by way of a simple axial pushing force. Instead, further actuation of the fluid receptacle 16A relative to the body portion 18B is achieved by rotation of the receptacle 16A. In this manner, the formations 78 slide between the formations 72 and cause a gradual, controlled axial actuation of the fluid receptacle 16A along the body portion 18B of the needle holder.

The end 52 of the needle 52 enters into the bung material 48 and starts to pass there-through. Further rotation of the fluid receptacle 16A causes the needle end 52 to puncture the bung 48 such that the free end of the needle passes through the bung 48 and into the interior of the fluid receptacle.

The frictional engagement of the formations 78 within formations 72 serves to resist and jerking action that would otherwise be experienced upon puncturing the bung under the application of a linear pushing force.

The different diameters of the body sections 74 and 76 allow the body 18B to be used in conjunction with either conventional fluid receptacles, such as receptacle 16 of FIGS. 2 and 4, or else with a modified receptacle 16A shown in FIGS. 7 and 8. Accordingly, a conventional receptacle 16 can pass within the internal diameter of the helical formations 72 without interference therewith, so as to engage with the reduced diameter of section 76 in a linear manner.

The helical or threaded engagement between the receptacle collar and the needle holder body provides for greater control of actuation of the fluid receptacle. The reverse, in this embodiment, anticlockwise, rotation of the fluid receptacle can be used to retract the collar from the formations 72, after which point the receptacle can be pulled out of the body 18B in a linear manner.

Whilst the features of FIGS. 7 and 8 have been described in relation to a body member having grip formation 28 and guard members 38, it will be appreciated that the actuation formations described in FIGS. 7 and 8 rely on the internal geometry of the body member and could be applied to a body member which excludes the grip portion 28 or 28A and/or guard members and/or other external features of the body member, as shown in FIG. 8.

The features of any one of the embodiments described above should be considered to be applicable to any other embodiment wherever practicable.

Furthermore, whilst the embodiments above have been described in relation to phlebotomy applications for humans, it will be appreciated that the embodiments could also be used in veterinarian applications. The above devices are particularly adapted for the drawing of blood but may potentially be used for the drawing of other fluids from the body and/or the delivery of fluid to a blood, or other, vessel.

The invention claimed is:

1. A medical needle holder comprising:
 a generally hollow body which extends in a direction of first axis from a first end to a second end, the first end being shaped for reception of a needle therein and the second end being open, wherein the first axis is substantially aligned in use with the needle positioned in the first end of the body; and,
 a grip portion which is pivotably mounted to the body in an in-use condition;

a fastener arranged to releasably hold the grip portion in
    the in-use condition; and
a pair of guard members depending from the first end of
    the body on either side of the first axis and on an
    opposing side of the body to the grip portion,
wherein each guard member has a guide surface adapted
    to rest against a patient's skin in the in-use condition,
wherein each guide surface is angularly offset from the
    first axis to facilitate insertion of the needle and to
    support the needle in a predetermined orientation once
    inserted,
wherein the entire grip portion is pivotably mounted to the
    body such that the grip portion is rotatably actuable
    relative to the body upon release of the fastener
    between the in-use condition and a storage or disposal
    condition, and
wherein the guard members are integrally formed with the
    grip portion and actuable therewith.

2. The medical needle holder according to claim 1, wherein the grip portion extends outwardly from the body in a direction which is obliquely angled relative to the first axis.

3. The medical needle holder according to claim 1, wherein an angle subtended between the first axis and a leading edge of the grip portion is between 30° and 80°.

4. The medical needle holder according to claim 1, wherein in the storage or disposal condition the grip portion is disposed substantially forward of the first end of the body.

5. The medical needle holder according to claim 4, wherein the grip portion has opposing side walls which protrude from the first end of the body on either side of the first axis in the storage or disposal condition so as to define a partially enclosed space there-between for at least partially enclosing the needle in the needle holder.

6. The medical needle holder according to claim 4, wherein the grip portion is pivotably or slidably mounted to the body for actuation between the in-use condition and the storage or disposal condition.

7. The medical needle holder according to claim 4, wherein the needle holder comprises a non-return mechanism comprising a ramped surface to prevent movement from the storage or disposal condition into the in-use condition.

8. The medical needle holder according to claim 1, wherein the grip portion depends from a vicinity of the first end of the body and extends towards the second end of the body.

9. The medical needle holder according claim 1, wherein the grip portion has one or more grip formations facing towards the first end of the body.

10. The medical needle holder according to claim 1, wherein each guide surface is angularly offset from the first axis by between 10° and 30°.

11. The medical needle holder according to claim 1, comprising one or more control formations on an inward facing surface of the body, the one or more control formations being shaped for cooperation with one or more corresponding formations on a fluid receptacle to be inserted into the body in use.

12. The medical needle holder according to claim 11, wherein the one or more control formations are arranged obliquely to the first axis so as to limit a degree of axial movement available to the fluid receptacle within the body.

13. The medical needle holder according to claim 11, wherein the one or more control formations are substantially helical in shape.

14. The medical needle holder according to claim 11, wherein the one or more control formations comprises a plurality of elongate control formations arranged about the first axis such that a leading edge of a first formation of the plurality of elongate control formations overlaps a trailing edge of a second adjacent formation of the plurality of elongate control formations.

15. The medical needle holder according to claim 5, wherein in the in-use condition, the opposing side walls extend beneath the body so as to define the pair of guard members.

16. The medical needle holder according to claim 1, wherein the grip portion and the pair of guard members are actuable relative to the body upon release of the fastener between the in-use condition and the storage or disposal condition in unison.

17. The medical needle holder according to claim 5, wherein in the in-use condition, the partially enclosed space receives at least a portion of the body between the opposing side walls but not a distal tip of the needle and wherein in the storage or disposal condition, the partially enclosed space is configured to receive the distal tip of needle.

18. The medical needle holder according to claim 1, the body comprising a pair of projections about which the grip portion is rotatable between the in-use condition and the storage or disposal condition.

19. A needle device comprising:
a needle holder comprising:
    a generally hollow body which extends in a direction of
        first axis from a first end to a second end, the first end
        being shaped for reception of a needle therein and
        the second end being open, wherein the first axis is
        substantially aligned in use with the needle positioned in the first end of the body; and,
    a grip portion which is pivotably mounted to the body
        in an in-use condition;
    a fastener arranged to releasably hold the grip portion
        in the in-use condition; and
    a pair of guard members depending from the first end
        of the body on either side of the first axis and on an
        opposing side of the body to the grip portion,
    wherein each guard member has a guide surface
        adapted to rest against a patient's skin in the in-use
        condition,
    wherein each guide surface is angularly offset from the
        first axis to facilitate insertion of the needle and to
        support the needle in a predetermined orientation
        once inserted,
    wherein the entire grip portion is pivotably mounted to
        the body such that the grip portion is rotatably
        actuable relative to the body upon release of the
        fastener between the in-use condition and a storage
        or disposal condition, and
    wherein the guard members are integrally formed with
        the grip portion and actuable therewith; and
a needle assembly attached to the needle holder part way
    along a length of the needle holder such that the needle
    extends substantially in the direction of the first axis
    from a free end which is outside of the body to an
    opposing end which is in the interior of the body.

20. A medical needle holder comprising:
a generally hollow body which extends in a direction of
    an axis from a first end to a second end, the first end
    being shaped for reception of a needle therein and the
    second end being open, wherein the axis is substantially aligned in use with the needle positioned in the
    first end of the body; and
a grip portion comprising a pair of spaced side walls
    defining a partially enclosed space there-between, wherein the entire grip portion is pivotably mounted to the body, wherein in an in-use condition, the grip portion extends toward the second end of the body, wherein in the in-use condition, the pair of side walls extend beneath the body so as to define a guard member beneath the body, the guard member adapted to rest against a patient's skin and to support the body in predetermined orientation on the patient's skin during use of the needle, wherein the grip portion and the guard member are configured to be rotatably actuable relative to the body in unison between the in-use condition and storage or disposal condition, wherein the needle holder comprises a releasable fastener for preventing movement of both the grip portion and the guard member in the in-use condition such that the needle holder can be stably held via the grip portion by a user whilst the body is supported on the patient's skin by the guard member, and wherein in the in-use condition, the partially enclosed space receives at least a portion of the body between the pair of side walls but not a distal tip of the needle, and wherein in the storage or disposal condition, the partially enclosed space is configured to receive the distal tip of the needle.

\* \* \* \* \*